United States Patent [19]

Distler et al.

[11] Patent Number: 4,571,495

[45] Date of Patent: Feb. 18, 1986

[54] MEASUREMENT SYSTEM UNIT FOR A COMPUTER TOMOGRAPH

[75] Inventors: Walter Distler, Erlangen; Fritz Peter, Buckenhof, both of Fed. Rep. of Germany

[73] Assignee: Siemens Aktiengesellschaft, Berlin and Munich, Fed. Rep. of Germany

[21] Appl. No.: 583,912

[22] Filed: Feb. 27, 1984

[30] Foreign Application Priority Data

Mar. 24, 1983 [DE] Fed. Rep. of Germany ... 8308842[U]

[51] Int. Cl.⁴ .............................................. G01J 1/42
[52] U.S. Cl. ........................................ 250/394; 378/4
[58] Field of Search .................. 250/366, 367, 370.01, 250/370.08, 370.09, 385, 394; 378/4

[56] References Cited

U.S. PATENT DOCUMENTS 4,119,853 10/1978 Shelley et al. ...................... 250/385
4,338,521 7/1982 Shaw et al. ......................... 250/367
4,490,614 12/1984 Peerenboom et al. .............. 250/385

Primary Examiner—Janice A. Howell
Attorney, Agent, or Firm—Mark H. Jay

[57] ABSTRACT

A measurement system unit for a tomography computer in which individual detectors are connected with corresponding channel electronic systems directly, that is, without the need for a cable. For this purpose, a carrier plate is provided, on one side of which the individual detectors are mounted, and on the other side of which are mounted a series of electronic boards. Each of the electronic boards carries the channel electronic system of the detector that is located opposite to it. On the carrier plate there can be fastened a printed circuit board which partially covers it. The electronic boards are connected mechanically and electrically with the carrier plate and mechanically and electrically with the printed circuit board.

3 Claims, 2 Drawing Figures

MEASUREMENT SYSTEM UNIT FOR A COMPUTER TOMOGRAPH

BACKGROUND OF THE INVENTION

This invention is related to a measurement system unit for a computer tomograph with a holder for a number of individual detectors as well as a channel electronics system assigned to each individual detector.

A measurement system unit of this kind is described in European patent application No. 81 103 494.1. In this familiar measurement system unit the individual detectors are mounted on a carrier plate from which a connecting cable leads to the channel electronics system. This connecting cable can fail on occasion which may be due to problems in the cable itself as well as to an inadequate connection to the detectors and the channel electronic system.

SUMMARY OF THE INVENTION

It is an object of the present invention to provide a measuring system unit of the type described above which offers a disturbance-free transmission of the signal from the individual detectors to the channel electronic system.

This and other objects are achieved according to the invention by means of a holder or a carrier plate, on one side of which the individual detectors are mounted and on the other side of which are mounted a series of electronic boards, each of which carries the channel electronic system of the detector that is located opposite to it. In the measuring system unit in accordance with the invention, each individual detector can be connected directly with the associated electronic system, by means of a printed circuit board, which can also consist of the carrier plate itself. Connecting cables between the individual detectors and the channel electronic systems can thus be eliminated. A particularly useful embodiment consists in having a printed circuit board fastened to the carrier plate and partially covering it and having the electronic boards connected partly mechanically and electrically with the carrier plate and partly mechanically and electrically with the printed circuit board. In this embodiment, the individual detectors are connected by means of electrical plug connections to the channel electronic systems arranged on the electronic boards. The connection to the outside is made by means of the printed circuit board, which is likewise connected to the electronic boards by means of plug connections and can be provided with socket contacts at its ends.

Other features and advantages of the invention will be apparent from the following description of the preferred embodiments, and from the claims.

For a full understanding of the present invention, reference should now be made to the following detailed description of the preferred embodiments of the invention and to the accompanying drawings.

DETAILED DESCRIPTION

Figure 1:
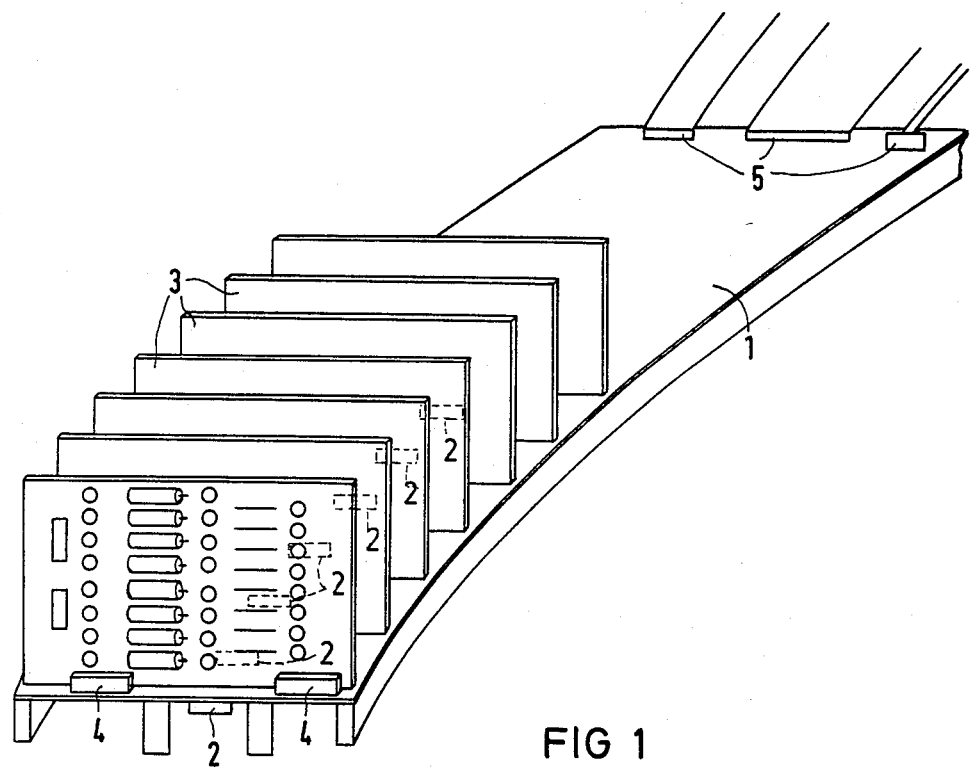
FIG. 1 shows a preferred embodiment of a measuring system unit in accordance with the invention.

FIG. 1 shows a curved circuit board 1, which serves as the carrier plate for a number of individual detectors of a tomography computer. One of the detectors which is designated by reference numeral 2 is shown. For each of the individual detectors on the printed circuit board 1, which is designed as the carrier plate, a channel electronic system, which is mounted on an electronic board, is provided on the other side of the circuit board 1. In FIG. 1 the electronic boards are designated by 3.

FIG. 1 shows that the printed circuit board 1 has on its bottom side the individual detectors 2 and on its top side the electronic boards 3 and that the electrical connection of the components 2 and 3 with the printed circuit board 1 have been made directly, that is, without the need for an electrical cable. For this purpose, the electronic boards 3 are connected with plug connections 4 with the printed circuit board 1. At the end of the printed circuit board 1, electrical connectors 5 have been provided for the transmission of the output signals of the electronic boards 3 via suitable cables.

Figure 2:
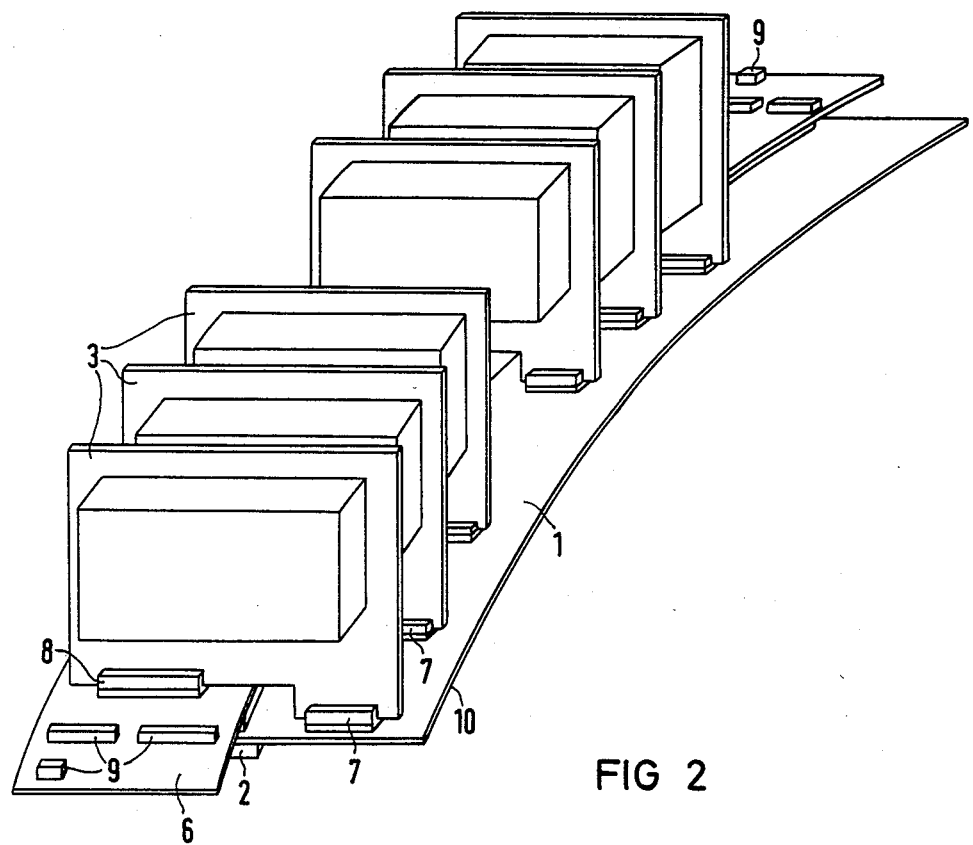
FIG. 2 shows a variant of the measuring system unit in accordance with FIG. 1.

In the embodiment according to FIG. 2 a printed circuit board 6 is fastened to the carrier plate 10 and partially covers it, and the electronic boards 3 are connected partly mechanically and electrically by means of plug connections 7 with the carrier plate 10 and partly mechanically and electrically by means of plug connections 8 with the printed circuit board 6. The transmission of signals from the individual detectors 2 to the corresponding electronic systems is accordingly accomplished by the plug connections 7. The output signals from the electronic boards 3 can be transmitted by the plug connections 8 to the electrical connectors 9 at the ends of the printed circuit board 6. From there they can be further transmitted with the help of cables.

There has thus been shown and described a novel measurement system unit for a tomography computer which fulfills all the objects and advantages sought therefor. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. In a measuring sytem unit for a tomography computer having a holder for carrying a plurality of individual detectors, as well as a channel electronic system assigned to each individual detector, the improvement wherein said holder comprises a carrier plate on one side of which the individual detectors are mounted, and on the other side of which are mounted a plurality of electronic boards, each of said electronic boards carrying the channel electronic system of a respective one of said detectors that is located opposite to it.

2. Measuring system unit in accordance with claim 1, wherein said carrier plate is a printed circuit board through which connections between each of said detectors and its assigned channel electronic system are effected.

3. Measuring system unit in accordance with claim 1, further comprising a printed circuit board, said board being fastened to said carrier plate and partially covering it, said electronic boards being connected partially mechanically and electrically with said carrier plate and partially mechanically and electrically with said printed circuit board.

* * * * *